United States Patent
Kyono et al.

(10) Patent No.: US 9,608,148 B2
(45) Date of Patent: Mar. 28, 2017

(54) SEMICONDUCTOR ELEMENT AND METHOD FOR PRODUCING THE SAME

(71) Applicant: Sumitomo Electric Industries, Ltd., Osaka-shi (JP)

(72) Inventors: Takashi Kyono, Itami (JP); Kei Fujii, Itami (JP); Katsushi Akita, Itami (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 0 days.

(21) Appl. No.: 14/615,217

(22) Filed: Feb. 5, 2015

(65) Prior Publication Data
US 2015/0144876 A1 May 28, 2015

Related U.S. Application Data
(62) Division of application No. 14/285,305, filed on May 22, 2014.

(30) Foreign Application Priority Data
May 31, 2013 (JP) .................................. 2013-115757

(51) Int. Cl.
H01L 31/0352 (2006.01)
H01L 21/02 (2006.01)
(Continued)

(52) U.S. Cl.
CPC ..... *H01L 31/035236* (2013.01); *G01N 23/20* (2013.01); *H01L 21/0262* (2013.01); *H01L 21/02398* (2013.01); *H01L 21/02463* (2013.01); *H01L 21/02466* (2013.01); *H01L 21/02507* (2013.01); *H01L 21/02546* (2013.01);
(Continued)

(58) Field of Classification Search
CPC ........ H01L 31/10; H01L 21/205; H01S 5/343
See application file for complete search history.

(56) References Cited

U.S. PATENT DOCUMENTS

| 5,251,225 A | 10/1993 | Eglash et al. |
| 2002/0004253 A1 | 1/2002 | Ooi et al. |

(Continued)

FOREIGN PATENT DOCUMENTS

| CN | 1546944 A | 11/2004 |
| CN | 102534764 A | 7/2012 |

(Continued)

OTHER PUBLICATIONS

Office Action issued in U.S. Appl. No. 14/285,305, dated Mar. 31, 2015.
(Continued)

*Primary Examiner* — Fernando L Toledo
*Assistant Examiner* — Lawrence-Linh T Nguyen
(74) *Attorney, Agent, or Firm* — Venable LLP; Michael A. Santori; F. Brock Riggs

(57) ABSTRACT

A method for producing a semiconductor element includes a step of forming a multiple quantum well in which a GaSb layer and an InAs layer are alternately stacked on a GaSb substrate by MOVPE, wherein, in the step of forming a multiple quantum well, an InSb film is formed on at least one of a lower-surface side and an upper-surface side of the InAs layer so as to be in contact with the InAs layer.

6 Claims, 11 Drawing Sheets

(51) Int. Cl.
  *H01L 21/66* (2006.01)
  *H01L 31/18* (2006.01)
  *G01N 23/20* (2006.01)
  *H01L 31/0304* (2006.01)
  *H01L 27/146* (2006.01)

(52) U.S. Cl.
  CPC ........ *H01L 21/02549* (2013.01); *H01L 22/12* (2013.01); *H01L 27/14694* (2013.01); *H01L 31/03046* (2013.01); *H01L 31/184* (2013.01); *G01N 2223/611* (2013.01); *G01N 2223/615* (2013.01); *Y02E 10/544* (2013.01)

(56) References Cited

U.S. PATENT DOCUMENTS

| | | | |
|---|---|---|---|
| 2002/0140012 A1 | 10/2002 | Droopad | |
| 2009/0224228 A1* | 9/2009 | Razeghi | B82Y 20/00 257/21 |
| 2010/0051900 A1* | 3/2010 | Huffaker | B82Y 20/00 257/13 |
| 2012/0326122 A1* | 12/2012 | Fujii | C30B 25/183 257/14 |
| 2013/0248821 A1* | 9/2013 | Miura | B82Y 20/00 257/21 |

FOREIGN PATENT DOCUMENTS

| | | |
|---|---|---|
| JP | 2011-054915 A | 3/2011 |
| JP | 2012-009777 A | 1/2012 |
| WO | 2012/073934 A1 | 6/2012 |

OTHER PUBLICATIONS

X.B. Zhang et al., "Metalorganic chemical vapor deposition growth of high-quality InAs/GaSb type II superlattices on (001) GaAs substrates," Applied Physics Letters, vol. 88, pp. 072104-1-072104-3 (2006).

Y. Huang et al., "Epitaxial growth and characterization of InAs/GaSb and InAs/InAsSb type-II superlattices on GaSb substrates by metalorganic chemical vapor deposition for long wavelength infrared photodetectors," Journal of Crystal Growth, vol. 314, pp. 92-96 (2011).

Li-Gong Li et al., "Effect of growth temperature on surface morphology and structure of InAs/GaSb superlattices grown by metalorganic chemical vapor deposition," Journal of Crystal Growth, vol. 359, pp. 55-59 (2012).

H.J. Haugan et al., "Exploring optimum growth for high quality InAs/GaSb type-II superlattices," Journal of Crystal Growth, vol. 261, pp. 471-478 (2004).

Notification of First Office Action in counterpart Chinese Patent Application No. 201410239477.5, dated Sep. 1, 2016.

* cited by examiner $\omega/2\theta\,(s)$ $\omega/2\theta\,(s)$

SEMICONDUCTOR ELEMENT AND METHOD FOR PRODUCING THE SAME

CROSS REFERENCE TO RELATED APPLICATIONS

This application is a Divisional of U.S. patent application Ser. No. 14/285,305, filed May 22, 2014, which claims the benefit of Japanese Patent Application No. 2013-115757, filed May 31, 2013, all of which are incorporated by reference in its entirety.

BACKGROUND OF THE INVENTION

1. Field of the Invention

The present invention relates to a semiconductor element and a method for producing the semiconductor element, specifically, to a semiconductor element configured to absorb infrared light and a method for producing the semiconductor element.

2. Description of the Related Art

Infrared light ranging from the near-infrared region to the mid-infrared region corresponds to the absorption spectrum region relating to the environment and living bodies including animals and plants. Developments of photodetectors for such wavelength regions are underway. The developments are mainly directed to photodiodes having absorption layers containing III-V compound semiconductors. The developments each put emphasis on the production of an epitaxial wafer having high crystallinity for the purpose of suppressing dark current. For example, Japanese Unexamined Patent Application Publication No. 2011-054915 discloses an embodiment directed to the near-infrared region and including growth of an epitaxial layered body including an absorption layer having a type-II III-V compound semiconductor (InGaAs/GaAsSb) multiple quantum well (MQW) structure by metal-organic vapor phase epitaxy using only metal-organic sources (all metal-organic source MOVPE). Japanese Unexamined Patent Application Publication No. 2012-009777 discloses an embodiment directed to the mid-infrared region and including formation of an absorption layer having an InAs/GaSb multiple quantum well on a GaSb substrate particularly by molecular beam epitaxy (MBE). This document states that an InSb strain-compensating layer, which is not employed therein, may be employed for strain compensation. X. B. Zhang, et al. "Metalorganic chemical vapor deposition growth of high-quality InAs/GaSb type II superlattices on (001) GaAs substrates", Applied Physics Letters 88, 072104(2006) discloses a method of forming an InAs/GaSb multiple quantum well on a GaAs substrate by standard MOVPE. This document states that an InSb strain-compensating layer is the cause of formation of nanopipes and hence is not employed. Y. Huang, et al. "Epitaxial growth and characterization of InAs/GaSb and InAs/InAsSb type-II superlattices on GaSb substrates by metalorganic chemical vapor deposition for long wavelength infrared photodetectors", Journal of Crystal Growth 314, 92 (2011) discloses a method of forming, on a GaSb substrate, an InAs/GaSb multiple quantum well including a strain-compensating layer (layer constituted by combination of InAsSb and InGaSb) by standard MOVPE. Li-Gong Li, et al. "Effect of growth temperature on surface morphology and structure of InAs/GaSb superlattices grown by metalorganic chemical vapor deposition", Journal of Crystal Growth 359, 55 (2012) discloses a method of forming, on a GaSb substrate, an InAs/GaSb multiple quantum well including an AsSb-mixing-plane serving as a strain-compensating layer by standard MOVPE. H. J. Haugan, et al. "Exploring optimum growth for high quality InAs/GaSb type-II superlattices", Journal of Crystal Growth 261, 471 (2004) discloses an example of forming, on a GaSb substrate, an InAs/GaSb multiple quantum well including an InSb strain-compensating layer by MBE.

SUMMARY OF THE INVENTION

Regarding techniques for producing infrared photodiodes, the following four points are considered. In this description, MOVPE and metal-organic chemical vapor deposition (MOCVD) are understood as the same method.

(1) An InAs/GaSb multiple quantum well used for the mid-infrared region and formed on a GaSb substrate needs a strain-compensating layer of some type. This is because the difference in lattice constant between InAs and GaSb is large and hence a multiple quantum well constituted by InAs and GaSb alone causes relaxation of strain (generation of lattice defects such as dislocation).

(2) In such a case where an InAs/GaSb multiple quantum well is formed on a GaSb substrate, InSb can be deposited to form a strain-compensating layer by MBE.

(3) In the case of using MOVPE, it is difficult to use InSb as a strain-compensating layer and, for example, combination of plural material layers is used as an alternative to InSb. The main reason for this is that InSb has a low melting point of 527° C. and it is difficult to perform all the depositions at temperatures sufficiently lower than the melting point of InSb throughout MOVPE. However, use of plural material layers or AsSb-mixing-plane makes the process complicated, causing difficulties in quality control.

(4) There is an example of using a GaAs substrate, which has a lattice constant that is considerably different from those of pair layers of MQW formed thereon, without using any strain-compensating layer. However, as described in (1) above, this example has a high probability of the occurrence of relaxation of strain in the MQW, resulting in degradation of the crystalline quality.

An object of the present invention is to provide a semiconductor element including a type-II InAs/GaSb multiple quantum well that can be efficiently produced by metal-organic vapor phase epitaxy (MOVPE or MOCVD) and that has high crystallinity; and a method for producing the semiconductor element.

A method for producing a semiconductor element according to an embodiment of the present invention allows production of a semiconductor element including a III-V compound semiconductor layered body. This production method includes a step of forming a multiple quantum well in which a GaSb layer and an InAs layer are alternately stacked on a GaSb substrate by metal-organic vapor phase epitaxy, wherein, in the step of forming a multiple quantum well, an InSb film is formed on at least one of a lower-surface side and an upper-surface side of the InAs layer so as to be in contact with the InAs layer.

A semiconductor element according to an embodiment of the present invention is a semiconductor element including III-V compound semiconductors formed on a III-V compound semiconductor substrate. The semiconductor element includes a buffer layer disposed on the substrate; a first multiple quantum well disposed on the buffer layer, the first multiple quantum well including a GaSb layer and an InAs layer that are alternately stacked and a strain-compensating layer that is disposed on a lower-surface side or an upper-surface side of the InAs layer so as to be in contact with the InAs layer; and a second multiple quantum well including a GaSb layer and an InAs layer that are alternately stacked so as to be in contact with each other, the second multiple quantum well not including any strain-compensating layer on a lower-surface side or an upper-surface side of the InAs layer.

An embodiment of the present invention can efficiently provide, by metal-organic vapor phase epitaxy (MOVPE or MOCVD), a semiconductor element including a type-II InAs/GaSb multiple quantum well having high crystallinity. The InSb film, which has a small thickness of about 1 monolayer (ML), is described with the term "film"; however, it is sometimes described with another term "layer". For example, an expression of "InSb strain-compensating layer" is used. The thicknesses of an InAs layer, a GaSb layer, and an InSb film may be referred to as film thicknesses. Unless misunderstanding is caused, the terms "layer" and "film" are sometimes omitted.

DESCRIPTION OF THE PREFERRED EMBODIMENTS

Figure 1:
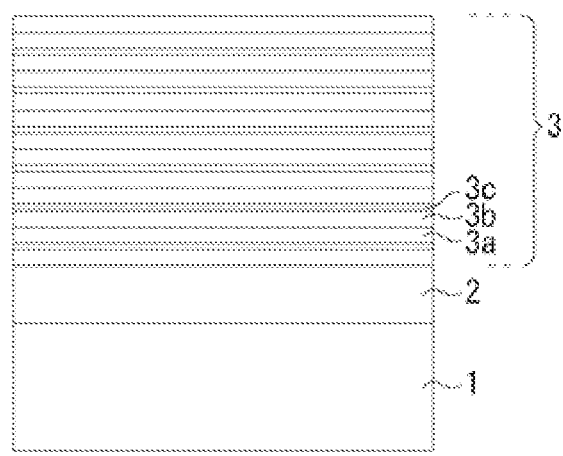
FIG. 1 illustrates an InAs/GaSb multiple quantum well including InSb strain-compensating layers in a photodiode that is a semiconductor element according to an embodiment of the present invention.

Hereinafter, features of embodiments of the present invention will be sequentially described.

1. Method for Producing Semiconductor Element

A method for producing a semiconductor element according to an embodiment of the present invention is a method for producing a semiconductor element including a III-V compound semiconductor layered body. This production method includes a step of forming a multiple quantum well in which a GaSb layer and an InAs layer are alternately stacked on a GaSb substrate by metal-organic vapor phase epitaxy; and, in this step of forming a multiple quantum well, an InSb film is formed on at least one of the lower-surface side and the upper-surface side of the InAs layer so as to be in contact with the InAs layer.

(1) GaSb and InAs

InAs has a lattice constant of 0.606 nm. GaSb has a lattice constant of 0.609 nm. InAs in an InAs/GaSb multiple quantum well is subjected to in-plane tensile strain and, without the presence of a strain-compensating layer, the lattice constant difference causes relaxation of strain at the interface between InAs and GaSb, resulting in introduction of lattice defects such as dislocation. In order to suppress the relaxation, InSb (lattice constant: 0.646 nm) is interposed between InAs and GaSb. In this case, InSb is interposed so as to have a film thickness of about 1 ML for the purpose of achieving strain compensation. In the production method of this embodiment, an InSb film is formed on the upper or lower surface of InAs of the type-II InAs/GaSb multiple quantum well. As a result, relaxation of strain at the interface between InAs and GaSb due to the lattice constant difference can be suppressed. Thus, generation of lattice defects such as dislocation is avoided. An InAs/GaSb multiple quantum well including InSb films preferably has a layered structure of 80 periods or more and 400 periods or less. Such a multiple quantum well having 80 periods or more can achieve sufficient optical absorption and exhibit sufficiently high sensitivity to mid-infrared light. Even when such a multiple quantum well is formed so as to have more than 400 periods, since the film thickness is more than the requirement for optical absorption, the sensitivity is not increased or tends to decrease; in addition, degradation of the crystallinity or a decrease in the throughput may be caused. In summary, the multiple quantum well is preferably formed so as to have a layered structure of 80 or more and 400 or less periods of InSb/InAs/GaSb or InAs/InSb/GaSb.

(2) InSb Strain-compensating Layer

There has been no example of achievement of high crystallinity in the formation of an InAs/GaSb multiple quantum well including an InSb strain-compensating layer by MOVPE. As described above, the main reason for this is probably that the melting point of InSb is a low temperature of 527° C., which is close to the growth temperatures of the multiple quantum well and layers thereon such as a window layer.

(3) Deposition Method

In an embodiment of the present invention, the multiple quantum well is formed by metal-organic vapor phase epitaxy (MOVPE). There is an example in which MBE is employed to form an InAs/GaSb multiple quantum well including an InSb strain-compensating layer. However, since MBE has low production efficiency, MOVPE suitable for mass production is employed for deposition. In MOVPE, it is important that the growth temperature is set to a value sufficiently lower than 527° C. Obviously, deposition may be performed by metal-organic vapor phase epitaxy using only metal-organic sources as source gases.

(4) Growth Temperature

The growth temperature is preferably set in the range of 430° C. or more and 500° C. or less. In this case, all the sources used are preferably organometallic compounds. At a growth temperature of 430° C. or more, such sources are efficiently decomposed and the atoms sufficiently migrate, resulting in high crystallinity. At a growth temperature of more than 500° C., InSb having a low melting point is less likely to deposit. Examples of Ga source include triethylgallium (TEGa) and trimethylgallium (TMGa). Examples of In (indium) source include trimethylindium (TMIn) and triethylindium (TEIn). Examples of As (arsenic) source include tertiarybutylarsine (TBAs) and trimethylarsenic (TMAs). Examples of Sb (antimony) source include trimethylantimony (TMSb), triethylantimony (TESb), triisopropylantimony (TIP Sb), trisdimethylaminoantimony (TDMASb), and tritertiarybutylantimony (TTBSb).

(5) First Growth Interruption

When the growth of an InAs layer is followed not by a first growth interruption but by the growth of an InSb film or a GaSb layer, As tends to enter the InSb film or the GaSb layer. This incorporation of As into the InSb film or the GaSb layer results in an increase in the tensile strain in the multiple quantum well. This may cause relaxation of strain accompanied by generation of dislocation. Such a problem can be addressed when the growth of an InAs layer is followed by the first growth interruption during which the As source and the like are discharged. For partial duration or the entire duration of the first growth interruption, supply of an Sb source can reduce the influence of the remaining gas containing As. The length of the growth interruption is preferably 3 seconds or more and 25 seconds or less. The growth interruption for 3 seconds or more provides the effect of suppressing incorporation of As. The growth interruption for more than 25 seconds may cause loss of As from the InAs layer.

(6) Second Growth Interruption

When growth interruption (second growth interruption) precedes the growth of an InAs layer, sharp composition change at the interface can be advantageously achieved. Sb tends to segregate in a surface or interface due to the surfactant effect. Accordingly, supply of an Sb source is not necessarily required for the purpose of protecting the surface of the InSb strain-compensating layer or the GaSb layer. Supply of an As source for partial duration or the entire duration of the second growth interruption allows smooth switching between source gases and the composition change at the interface can be made sharper. The length of the growth interruption is preferably 3 seconds or more and 25 seconds or less. The growth interruption for 3 seconds or more provides the effect of providing sharp composition change at the interface. The growth interruption for more than 25 seconds does not considerably enhance the effect.

(7) Problem in Production (Determination of Film Thicknesses in InAs/GaSb Multiple Quantum Well Including InSb Strain-compensating Layer)

In production, it is important to accurately control film thicknesses in an InAs/GaSb multiple quantum well including an InSb strain-compensating layer having a thickness of about 1 ML. In general, film thicknesses in a multiple quantum well are determined on the basis of X-ray diffraction (XRD) signals. However, in the measurement of a multiple quantum well including an InSb strain-compensating layer having a thickness of about 1 ML, in spite of different thickness configurations of three thin films, similar XRD signals are produced in some cases. Specifically, two thickness configurations (thickness of InAs layer, thickness of GaSb layer, and thickness of InSb strain-compensating layer) may be represented by, for example, (a1, b1, c1) and (a2, b2, c2); these (a1, b1, c1) and (a2, b2, c2) are actually different from each other, but sometimes provide similar X-ray diffraction signals, that is, appear to be similar in terms of XRD. Such a problem can be addressed by addition of a second InAs/GaSb multiple quantum well not including any InSb strain-compensating layer, to the same semiconductor element. This second InAs/GaSb multiple quantum well not including any InSb strain-compensating layer is referred to as "additional MQW layers for thickness check". This semiconductor element produces X-ray diffraction signals including a combination of X-ray diffraction signals of the first multiple quantum well including InSb strain-compensating layers (main MQW layers) and X-ray diffraction signals of the second multiple quantum well not including any InSb strain-compensating layer (additional MQW layers for thickness check). These additional MQW layers for thickness check do not include InSb and hence formation of a layered structure having a large number of periods results in relaxation of strain. Accordingly, the additional MQW layers for thickness check are formed so as to have about 10 periods or less. As a result, the X-ray diffraction signals derived from the additional MQW layers for thickness check are not strong and appear at the shoulder of a sharp peak derived from the main MQW layers. Such an X-ray diffraction profile (XRD profile) is not simple. However, utilization of computer simulation allows understanding of the overall film-thickness configuration constituted by the main MQW layers and the additional MQW layers for thickness check. That is, by utilizing computer simulation in agreement with such an XRD profile, accurate film thicknesses can be determined. In this case, the simulation is easily performed by employing the same film-thickness design for InAs/GaSb of the first multiple quantum well including InSb strain-compensating layers and for InAs/GaSb of the second multiple quantum well not including any InSb strain-compensating layer. The additional MQW layers for thickness check have 10 or less periods of InAs/GaSb. Accordingly, for example, addition of such MQW layers to a photodiode having main MQW layers (200 periods) merely causes negligible influences on the performance of the photodiode such as sensitivity.

2. Semiconductor Element (1) Layered Structure of First Multiple Quantum Well Including Strain-Compensating Layers and Second Multiple Quantum Well Not Including Any Strain-Compensating Layer As described in 1. (7) above, when a semiconductor element includes only the first multiple quantum well including strain-compensating layers (main MQW layers), the film thicknesses are not accurately determined on the basis of X-ray diffraction signals. However, when a semiconductor element has a layered structure of the main MQW layers and the second multiple quantum well not including any strain-compensating layer (additional MQW layers for thickness check), the film thicknesses can be accurately determined. The strain-compensating layers may be formed of, for example, InSb, InAsSb, or InGaSb.

(2) Second Multiple Quantum Well Not Including Any Strain-compensating Layer (Additional MQW Layers for Thickness Check)

The second multiple quantum well does not include any strain-compensating layer. Accordingly, when InAs layers and GaSb layers are formed so as to have very large thicknesses on a GaSb buffer layer, relaxation of strain and generation of dislocation may be caused. For this reason, the second multiple quantum well is preferably formed so as to have a thickness equal to or less than the critical thickness. In addition, since the second multiple quantum well does not include any strain-compensating layer, it is difficult to grow a large number of periods with high crystallinity. Thus, the second multiple quantum well not including any strain-compensating layer is preferably formed so as to have 4 periods or more and 10 periods or less. Formation of 4 or more periods allows identification of X-ray diffraction signals derived from the additional MQW layers for thickness check. Formation of 10 or less periods allows reduction of the probability of relaxation of strain.

(3) Substrate

The substrate is desirably a GaSb substrate allowing homoepitaxial growth of a GaSb buffer layer thereon. However, a GaSb buffer layer has a tendency of keeping a certain level of crystallinity even after heteroepitaxial growth involving lattice mismatch is performed and lattice relaxation is caused. For this reason, the substrate may be formed of another III-V compound semiconductor such as GaAs or InP. In this case, loss of absorption of mid-infrared light in the substrate can be reduced.

Hereinafter, specific examples of a semiconductor element and a method for producing the semiconductor element according to an embodiment of the present invention will be described with reference to drawings. The present invention is not limited to these examples. The scope of the present invention is indicated by Claims and is intended to embrace all the modifications within the meaning and range of equivalency of the Claims.

FIG. 1 illustrates, as a semiconductor element according to an embodiment of the present invention, a photodiode including a GaSb substrate 1, a GaSb buffer layer 2, and an InAs/GaSb multiple quantum well 3. The (001) GaSb substrate 1 is in contact with the undoped GaSb buffer layer 2 on which the InAs/GaSb multiple quantum well having 80 periods or more and including InSb films is disposed as an absorption layer 3. In this multiple quantum well 3, InAs layers 3a each have a thickness of, for example, about 2 nm; and GaSb layers 3b each have a thickness of, for example, about 4 nm. This InAs/GaSb multiple quantum well contains InSb strain-compensating layers 3c each having a film thickness of about 1 ML. As a result, the InAs layers 3a subjected to in-plane tensile strain can be prevented from relaxation of strain even when the number of periods is 80 or more, for example, 300. That is, the presence of the InSb strain-compensating layers 3c in the multiple quantum well suppresses relaxation of strain and generation of dislocation.

Figure 2:
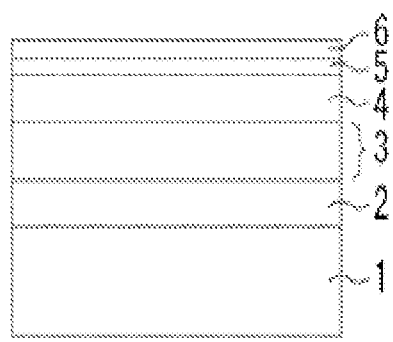
FIG. 2 illustrates an epitaxial wafer of a photodiode according to an embodiment of the present invention.

FIG. 2 is a sectional view illustrating an epitaxial wafer 10 including layers on the type-II multiple quantum well absorption layer 3. Specifically, a GaSb layer 4, a first InAs layer 5, and a second InAs layer 6 are disposed on the type-II InAs/GaSb multiple quantum well absorption layer 3.

Figure 3:
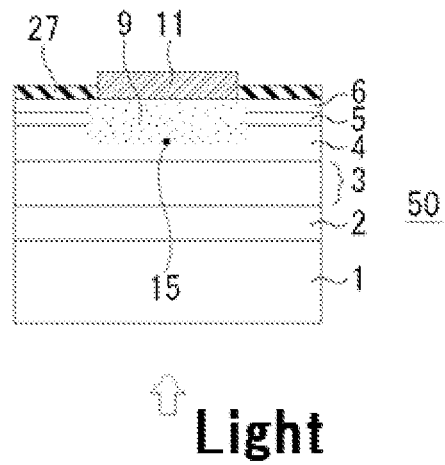
FIG. 3 illustrates a photodiode (single pixel) that is a semiconductor element according to an embodiment of the present invention.

FIG. 3 illustrates a planar photodiode 50 including a single pixel. Light enters the photodiode 50 through the back surface of a GaSb substrate 1. Tellurium (Te) serving as n-type impurity is introduced by selective area diffusion through the surface of a second InAs layer 6 into the second InAs layer 6, a first InAs layer 5, and a GaSb layer 4. Thus, an n-type region 9 is formed. For example, the Te concentration is $1\times10^{21}$ cm$^{-3}$ to $3\times10^{21}$ cm$^{-3}$ in the second InAs layer 6, $2\times10^{21}$ cm$^{-3}$ to $3\times10^{21}$ cm$^{-3}$ in the first InAs layer 5, and a lower concentration of $4\times10^{16}$ cm$^{-3}$ to $2\times10^{21}$ cm$^{-3}$ in the GaSb layer 4. A p-n junction 15 is formed in the front portion of the n-type region 9. A reverse bias voltage is applied to the p-n junction 15 by an n-electrode 11 and a p-electrode (not shown, serving as a ground electrode) to thereby form a depletion layer around the p-n junction 15. The p-electrode or the ground electrode can be disposed in ohmic contact with the back surface of the GaSb substrate 1 that is turned into a p-type substrate by being doped with a p-type impurity. Alternatively, while the GaSb substrate 1 may be a p-type or undoped substrate, the ground electrode (p-electrode) may be disposed in ohmic contact with a GaSb buffer layer 2 that is turned into a p-type layer. In order to reduce absorption loss in the GaSb substrate, the GaSb substrate may be thinned to a thickness of, for example, 40 to 100 μm by polishing or etching. A passivation film 27 is disposed around the n-electrode (pixel electrode) 11 so as to cover the second InAs layer 6. Thus, the planar photodiode serving as an example has been described. Alternatively, a mesa-type photodiode may be formed by doping the upper InAs layer with an n-type impurity and by performing wet etching or dry etching to provide discrete elements.

Figure 4:
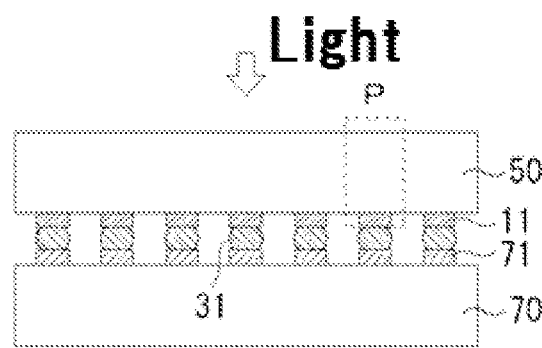
FIG. 4 illustrates an optical sensor device including a photodiode array integrated with a complementary metal oxide semiconductor (CMOS) serving as a read-out integrated circuit.

FIG. 4 illustrates an optical sensor device 90 including a photodiode 50 including an array of plural absorption portions or pixels P. The photodiode 50 is integrated with a complementary metal oxide semiconductor (CMOS) 70 serving as a read-out integrated circuit (ROIC) to constitute the optical sensor device 90 such as an image pickup device. Each of the pixels P in FIG. 4 corresponds to the single-pixel photodiode in FIG. 3. Receiving of light in a depletion layer formed around the p-n junction 15 results in generation of electron-hole pairs. The holes drift to the ground electrode that is the p-electrode, whereas electrons drift to the n-electrode (pixel electrode) 11. These charges generated upon receiving of light are read out by read-out electrodes 71 of the CMOS 70 at a predetermined scanning pitch. On the basis of the magnitudes of charges, contrast is determined and, for example, an image is formed. The conductive connection between each pixel electrode 11 and its corresponding read-out electrode 71 is ensured through a bump 31.

Figure 5:
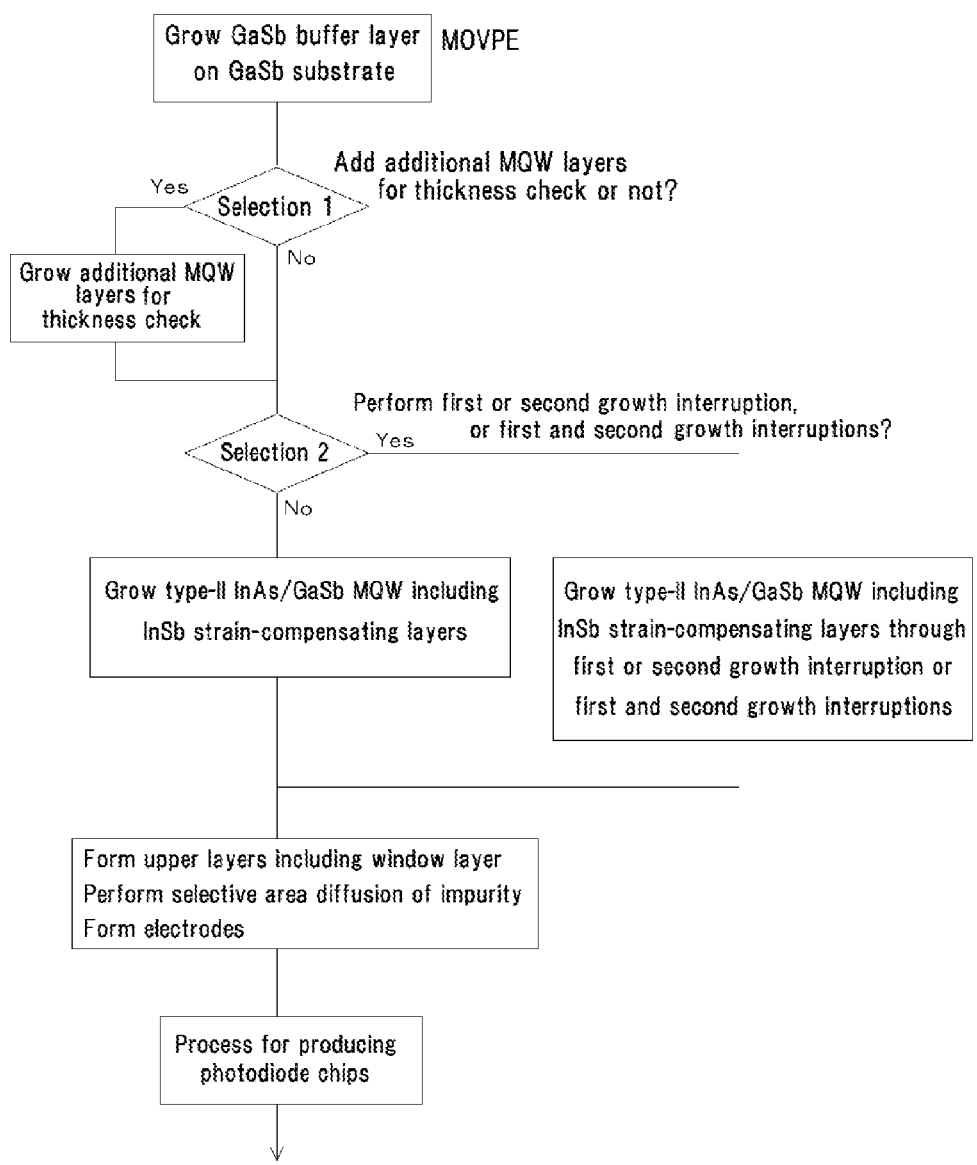
FIG. 5 is a flow chart for producing a photodiode.

FIG. 5 is a flow chart of a method for producing a photodiode of the embodiment. A GaSb substrate 1 is placed within a MOVPE growth chamber and a GaSb buffer layer 2 is grown on the GaSb substrate 1. Unless the GaSb substrate 1 is doped with a p-type impurity such as Zn, the GaSb buffer layer 2 is doped with such a p-type impurity for the purpose of forming a p-electrode in ohmic contact with the GaSb buffer layer 2. Alternatively, the buffer layer 2 may be formed as an undoped layer; instead, the GaSb substrate 1 may be doped with a p-type impurity and a p-electrode is formed in ohmic contact with the substrate 1. Subsequently, at Selection 1, whether additional MQW layers 3k for thickness check are added or not is decided. The additional MQW layers 3k for thickness check are constituted by a multiple quantum well that has 4 or more and 10 or less periods of InAs layer 3a/GaSb layer 3b and that does not have any InSb strain-compensating layer 3c. In the case where the additional MQW layers 3k for thickness check are added, these layers 3k are grown on the GaSb buffer layer 2. A first multiple quantum well 3 (main MQW layers) that includes about 100 periods of InAs layer 3a/GaSb layer 3b and includes InSb strain-compensating layers 3c is grown so as to be in contact with the additional MQW layers 3k for thickness check. In the case where the additional MQW layers 3k for thickness check are not added, the main MQW layers 3 are directly grown on the GaSb buffer layer 2.

At Selection 2, selection is made from, during the growth of the multiple quantum well 3, "the first growth interruption after growth of an InAs layer, the second growth interruption before growth of an InAs layer, or the first and second growth interruptions are performed" and "the growth interruptions are not performed". Regardless of whether at least one growth interruption is performed or no growth interruptions are performed, the main MQW layers 3 are preferably grown under the following conditions: only metal-organic sources are used and the multiple quantum well is grown at a growth temperature of 430° C. or more and 500° C. or less. In this case, the multiple quantum well serving as the absorption layer 3 can be grown at a temperature that is sufficiently lower than the melting point (527° C.) of the InSb strain-compensating layers 3c. As a result, the InSb layers are formed so as to have high crystallinity and are also expected to sufficiently provide the effect of strain compensation. The effects of the first and second growth interruptions will be specifically described in Examples. After growth of the main MQW layers 3 including 80 or more and 400 or less periods of InAs/GaSb and including the InSb strain-compensating layers 3c, for example, the following processes are performed: growth of layers (upper layers including a window layer) on the absorption layer 3; introduction of an n-type impurity through an epitaxial-layer surface by selective area diffusion; and formation of electrodes. That is, such final structures for the planar photodiode are formed by known techniques.

In the growth of the additional MQW layers 3k for thickness check, the first growth interruption, the second growth interruption, or the first and second growth interruptions may also be performed (which is not described above for the purpose of providing simple explanation).

EXAMPLE 1

Investigation of Effect of InSb Strain-compensating Layer in Multiple Quantum Well (InAs/GaSb)

In the growth of a type-II multiple quantum well (InAs/GaSb) by MOVPE, the crystallinity of the multiple quantum well was investigated in terms of comparison between the case of the presence of InSb strain-compensating layers 3c and the case of the absence of InSb strain-compensating layers 3c. The samples used were Sample A1 including InSb strain-compensating layers 3c and Sample B1 not including any InSb strain-compensating layer. A GaSb buffer layer 2 was grown on a GaSb substrate 1. Subsequently, a type-II multiple quantum well including 100 periods (InAs layer 3a and GaSb layer 3b) including the InSb strain-compensating layers 3c was grown to provide Sample A1; alternatively, the same multiple quantum well except for the absence of the InSb strain-compensating layers 3c was grown to provide Sample B1. The growth conditions were as follows.

(1) The undoped GaSb buffer layer 2 was grown to a thickness of 100 nm on the Te-doped GaSb substrate 1 at a growth temperature of 500° C.

(2) The growth temperature was decreased to 475° C. and 100 periods (2-nm InAs layer 3a and 4-nm GaSb layer 3b) including the InSb strain-compensating layers 3c each having a thickness of 0.2 nm were grown to provide Sample A1. Each InSb strain-compensating layer 3c was disposed under its corresponding InAs layer 3a.

Figure 6:
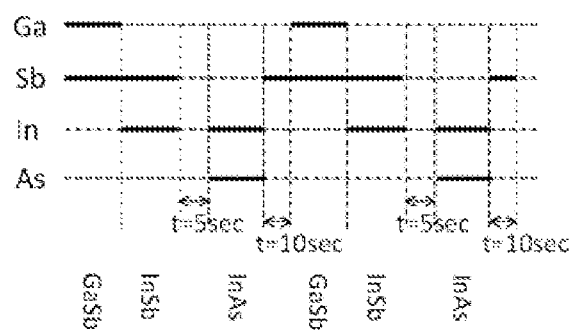
FIG. 6 illustrates a pattern when source gases are supplied during growth of an InAs/GaSb multiple quantum well including InSb strain-compensating layers in Example 1.

(3) During the growth of 100 periods (2-nm InAs layer 3a and 4-nm GaSb layer 3b), as illustrated in FIG. 6, the first growth interruption was performed after the growth of the InAs layer 3a and before the growth of the GaSb layer 3b; and the second growth interruption was performed after the growth of the InSb layer 3c and before the growth of the InAs layer 3a. During the first growth interruption, the growth was interrupted for 10 seconds while an Sb source was supplied. During the second growth interruption, the growth was interrupted for 5 seconds while no group V sources were supplied.

(4) Sample B1 serving as a comparative example was also prepared by growing 100 periods (2-nm InAs layer and 4-nm GaSb layer) not including any InSb strain-compensating layer. During the preparation of Sample B1, the first and second growth interruptions were respectively performed after and before the growth of InAs layer, which was the same as in Sample A1.

Figure 7:
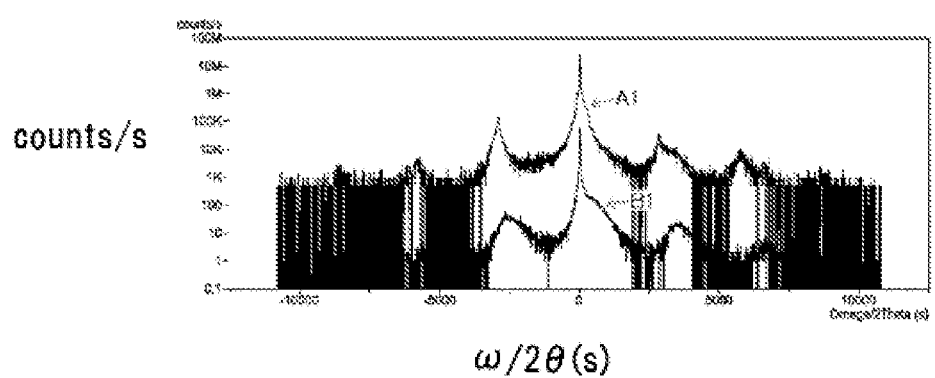
FIG. 7 illustrates X-ray diffraction (XRD) profiles of Sample A1 (including InSb strain-compensating layers) and Sample B1 (not including any InSb strain-compensating layer) in Example 1.

FIG. 7 illustrates XRD profiles of (004) plane of Samples A1 and B1. In FIG. 7, Sample A1 exhibits a sharper satellite peak than Sample B1. This means that, in Sample A1 (invention example), the InSb strain-compensating layers compensate for the strain and, even after the growth of 100 periods, disorder of the crystalline structure is suppressed. Sample A1 (invention example) was also subjected to photoluminescence (PL) evaluation and a peak was detected at a wavelength of 3.8 µm at a temperature of 4 K. Thus, incorporation of the multiple quantum well of Sample A1 into a photodiode can provide an optical sensor device (for example, in FIG. 4) having a cutoff wavelength corresponding to the above-described wavelength. This PL wavelength or optical absorption wavelength can be changed within the range of 3 to 12 µm by controlling film thicknesses in the multiple quantum well (InAs layer/GaSb layer). In contrast to Sample A1, as expected, Sample B1 provided the following results: since Sample B1 did not include any InSb strain-compensating layer, the satellite peak in the XRD profile in FIG. 7 is wide and dull, which shows that relaxation of strain or the like probably occurred in the InAs/GaSb multiple quantum well.

EXAMPLE 2

Influence of Film Thickness of InSb Strain-compensating Layer

In order to demonstrate the effect of the InSb strain-compensating layers 3c, multiple quantum wells were prepared that were modified from the multiple quantum well in Example 1 such that the number of periods was decreased from 100 to 6. Such multiple quantum wells having 6 periods were used to investigate the influence of film thickness of the InSb strain-compensating layers 3c. The reason for decreasing the number of periods of the multiple quantum wells in this investigation is as follows: even when InSb layers having a small film thickness do not provide sufficient strain compensation, a multiple quantum well having a thickness equal to or less than the critical thickness retains its structure; and, as a result, appropriate comparison and evaluation can be performed. Samples having the structure illustrated in FIG. 1 were produced so as to have different thicknesses of the InSb strain-compensating layers 3c under the same growth conditions as in Example 1.

Specifically, the following three Samples were prepared.

Sample A2: InSb strain-compensating layers 3c each had a thickness of 0.1 nm.

Sample A3: InSb strain-compensating layers 3c each had a thickness of 0.5 nm.

Sample A4: InSb strain-compensating layers 3c each had a thickness of 1.0 nm.

Figure 8:
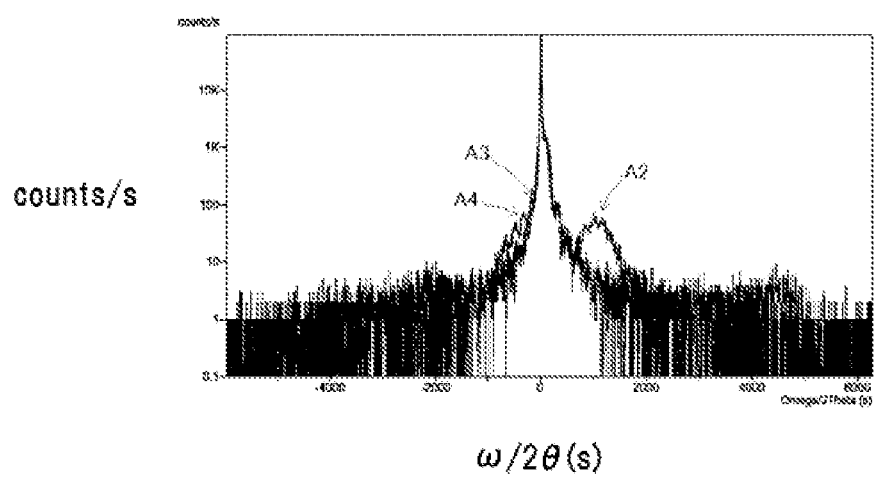
FIG. 8 illustrates XRD profiles indicating the influence of the thickness of InSb strain-compensating layers formed in an InAs/GaSb multiple quantum well in Example 2.

FIG. 8 collectively illustrates the XRD profiles of these Samples. In FIG. 8, as the thickness of InSb strain-compensating layers 3c increases, the zeroth-order peak shifts to the peak (central peak) derived from the GaSb substrate 1. This result shows the presence of InSb films successfully grown by MOVPE. This result also shows that, as intended, InSb exerts the effect of compensation for strain in the growth of the InAs/GaSb multiple quantum well. The result also shows that the InSb strain-compensating layers desirably have a thickness of 0.4 to 2 ML.

EXAMPLE 3

Effect of Growth Interruption After Growth of InAs (First Growth Interruption)

The effect of growth interruption after growth of InAs (first growth interruption) was demonstrated. Samples were prepared such that InAs/GaSb multiple quantum wells did not include any InSb strain-compensating layer. Accordingly, for the same reason as in Example 2, each InAs/GaSb multiple quantum well was formed so as to have 6 periods. Since 6 periods correspond to a thickness equal to or less than the critical thickness, relaxation of strain does not occur. In Example 3, during growth interruption after growth of InAs (first growth interruption), the carrier gas was continuously supplied, but source gases were not supplied.

Figure 9:
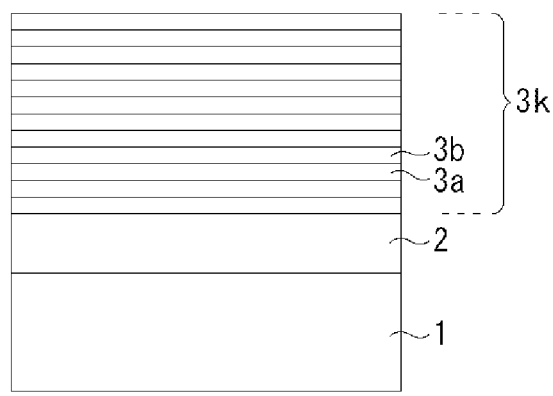
FIG. 9 illustrates a Sample used for demonstrating the effect of growth interruption (first growth interruption) performed after growth of an InAs layer in Example 3.
Figure 10:
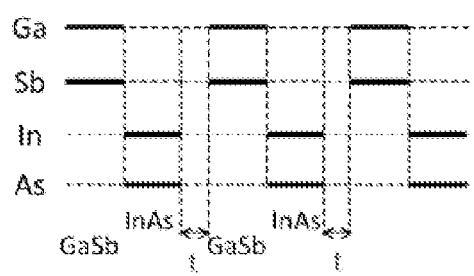
FIG. 10 illustrates a pattern when source gases are supplied that relates to the first growth interruption during growth of an InAs/GaSb multiple quantum well in Example 3.

FIG. 9 illustrates the structure of such Sample. An InAs/GaSb multiple quantum well 3k not including any InSb strain-compensating layer is disposed on an undoped GaSb buffer layer 2. This InAs/GaSb multiple quantum well 3k not including any InSb strain-compensating layer has 6 periods and corresponds to additional MQW layers for thickness check. Referring to FIG. 10, time t for growth interruption after growth of InAs (first growth interruption) was varied in the range of 0 to 10 seconds. Specifically, the following three Samples were prepared.

Sample A5: the time for first growth interruption was 0 seconds.

Sample A6: the time for first growth interruption was 5 seconds.

Sample A7: the time for first growth interruption was 10 seconds.

Figure 11:
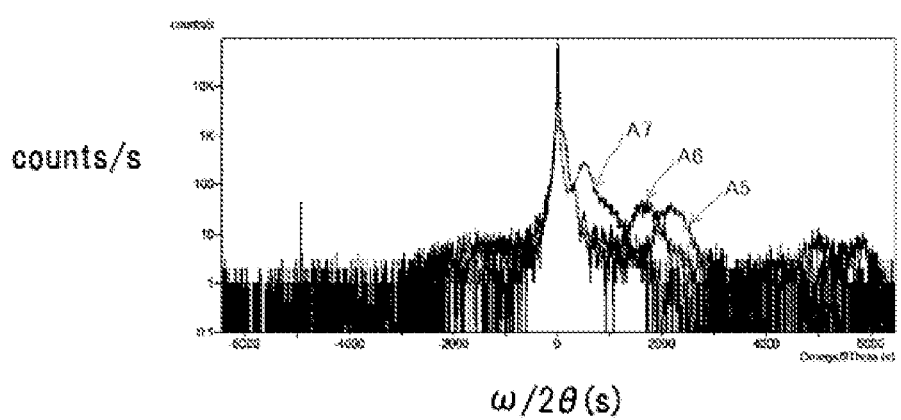
FIG. 11 illustrates XRD profiles indicating the influence of the length of first growth interruption during growth of an InAs/GaSb multiple quantum well in Example 3.

FIG. 11 collectively illustrates the XRD profiles of these Samples. In FIG. 11, as the time for the growth interruption after growth of InAs 3a increases, the zeroth-order peak shifts toward the peak of the GaSb substrate. Regarding the XRD profile of Sample A7 in which the time for growth interruption was 10 seconds, film thicknesses in a multiple quantum well providing this profile were calculated by simulation and found to be GaSb (3.7 nm)/InAs (2.0 nm). That is, Sample A7 in which the time for growth interruption was 10 seconds had film thicknesses close to the designed thicknesses. In contrast, in Sample A5 in which the time for growth interruption was 0 seconds, tensile strain in the multiple quantum well was larger than the intended strain and the layers formed were probably not GaSb (intended) but GaSbAs. This result means that no growth interruption (0 seconds) after growth of the InAs layer 3a is insufficient for preventing incorporation of As into the GaSb layer 3b formed after growth of the InAs layer 3a. By appropriately performing growth interruption after growth of the InAs layer 3a, the influence of the remaining gas containing As is reduced, so that almost ideal switching of gases can be achieved. Thus, the growth interruption results in enhancement of the sharpness of composition change at the InAs/GaSb interface and also small strain in the multiple quantum well, which is advantageous in the case of increasing the number of periods.

EXAMPLE 4

Influence of Supply of Source Gas During Growth Interruption After Growth of InAs (First Growth Interruption)

Figure 12:
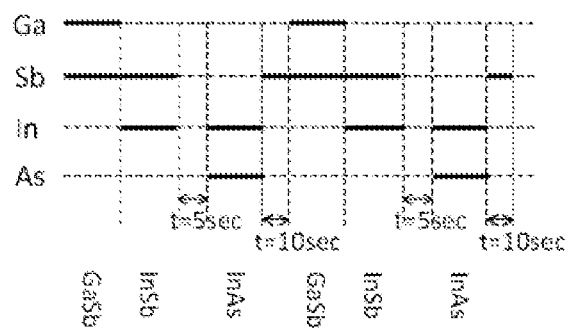
FIG. 12 illustrates a pattern when source gases are supplied during growth of an InAs/GaSb multiple quantum well including InSb strain-compensating layers in Example 4.

In Example 3, source gases were not supplied during the first growth interruption. Two Samples used in Example 4 for demonstration of influence of supply of source gas were the same as in Example 1. That is, each Sample had the structure illustrated in FIG. 1 and had a 100-period InAs/GaSb multiple quantum well including InSb strain-compensating layers 3c. In the two Samples, 100-period InAs/GaSb multiple quantum wells including InSb strain-compensating layers 3c were grown at a growth temperature of 450° C. The film-thickness configuration was different from that of Example 1: InAs and GaSb were formed so as to have thicknesses of 4 nm and 2 nm, respectively; and the InSb strain-compensating layers 3c were formed so as to have a thickness of 0.3 nm. As illustrated in FIG. 12, the growth interruption after growth of InAs (first growth interruption) was performed for 10 seconds and the growth interruption before growth of InAs (second growth interruption) was performed for 5 seconds. Specifically, the following two Samples were prepared.

Sample A8: during 10 seconds of the growth interruption after growth of InAs (first growth interruption), Sb source gas was supplied.

Sample A9: during 10 seconds of the growth interruption after growth of InAs (first growth interruption), source gases were not supplied.

Figure 13:
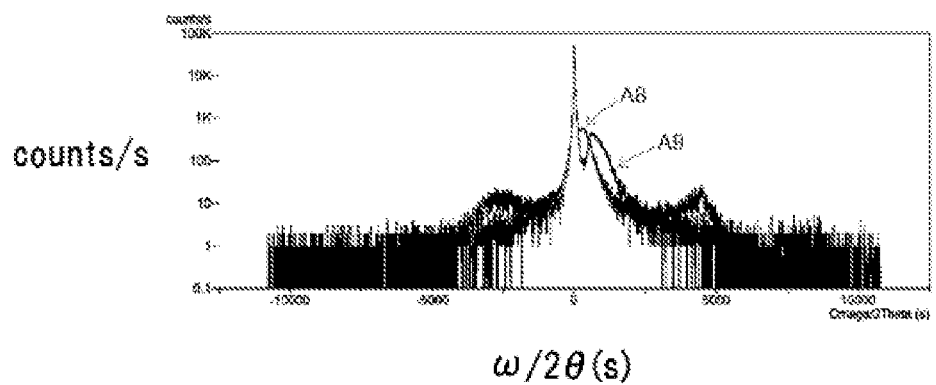
FIG. 13 illustrates XRD profiles indicating the influence of supply of a source gas during the first growth interruption in growth of an InAs/GaSb multiple quantum well in Example 4.

FIG. 13 illustrates the XRD profiles of the two Samples. The zeroth-order peak of Sample A8 is obviously located closer to the peak of the GaSb substrate than the zeroth-order peak of Sample A9. In Sample A9, incorporation of As into GaSb still occurred. In contrast, in Sample A8, an Sb source was continuously supplied during the first growth interruption (10 seconds), so that remaining As was effectively discharged. In Sample A9, strain compensation was not sufficiently provided; however, ±first-order satellite peaks were clearly observed, compared with Sample A8. This result indicates that an excess of Sb source during the first growth interruption may cause segregation of Sb in an epitaxial-layer surface, resulting in degradation of the sharpness of interfacial composition change. In order to achieve both suppression of incorporation of As and suppression of segregation of Sb, it is probably effective to supply the source gas not for the entire duration of the first growth interruption but for partial duration of the first growth interruption.

EXAMPLE 5

Effect of Growth Interruption Before Growth of InAs (Second Growth Interruption)

Figure 14:
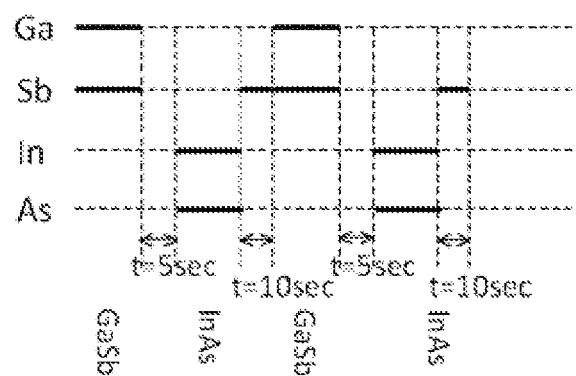
FIG. 14 illustrates a pattern when source gases are supplied in the investigation of the effect of growth interruption (second growth interruption) performed before growth of InAs in Example 5.

On the basis of the case where the first growth interruption was performed for 10 seconds in Example 3, the effect of growth interruption before growth of InAs (second growth interruption) was demonstrated. In Example 5, as illustrated in FIG. 14, the effect of performing, in addition to the first growth interruption for 10 seconds, the second growth interruption (growth interruption before growth of InAs) for 5 seconds was investigated. Specifically, the following two Samples were prepared.

Sample A10: the first growth interruption (10 seconds) alone was performed, whereas the second growth interruption was not performed.

Sample A11: the first and second growth interruptions illustrated in FIG. 14 were performed.

Figure 15A:
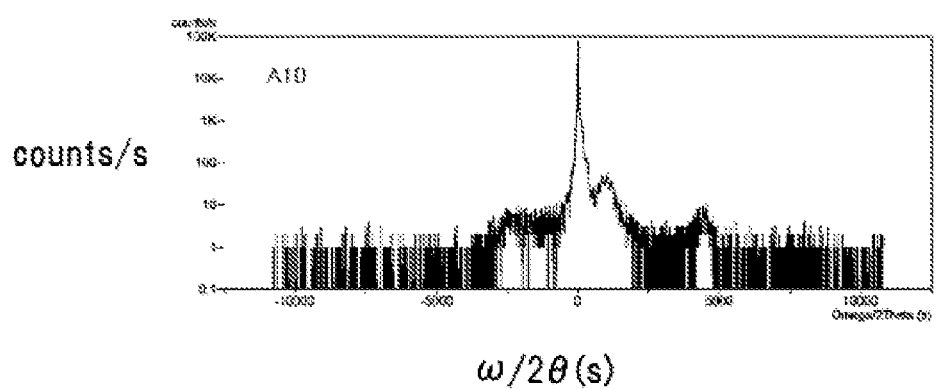
FIG. 15A illustrates the XRD profile of an InAs/GaSb multiple quantum well formed without performing a second growth interruption.
Figure 15B:
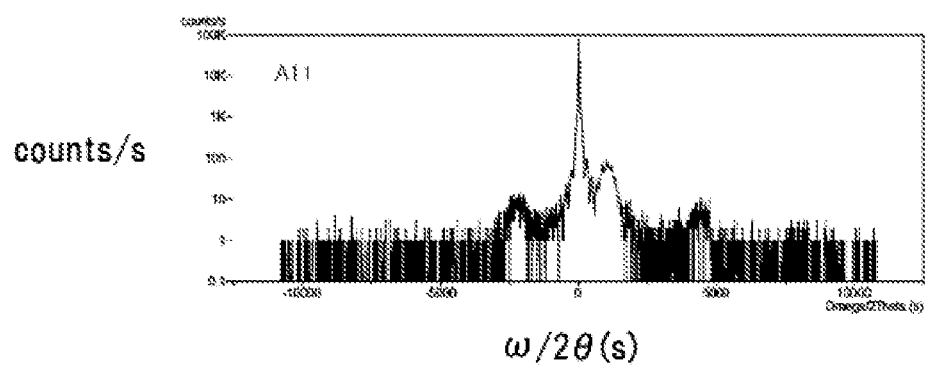
FIG. 15B illustrates the XRD profile of an InAs/GaSb multiple quantum well formed through a second growth interruption for 5 seconds.

FIG. 15A illustrates the XRD profile of Sample A10. FIG. 15B illustrates the XRD profile of Sample A11. In Sample A11 in which the second growth interruption for 5 seconds was added, the satellite peak in the XRD profile is sharpened. That is, the satellite peak stands out more clearly in FIG. 15B than in FIG. 15A. This result suggests that sharp switching of source gases causes enhancement of crystallinity of the periodic structure and sharpness of interfacial composition change. In FIGS. 15A and 15B, the positions of the satellite peaks are almost the same. Accordingly, unintended incorporation of element such as incorporation of As observed in Example 3 is not caused.

EXAMPLE 6

Determination of Film Thicknesses in Multiple Quantum Well (Effect of Additional MQW Layers for Thickness Check)

Figure 16:
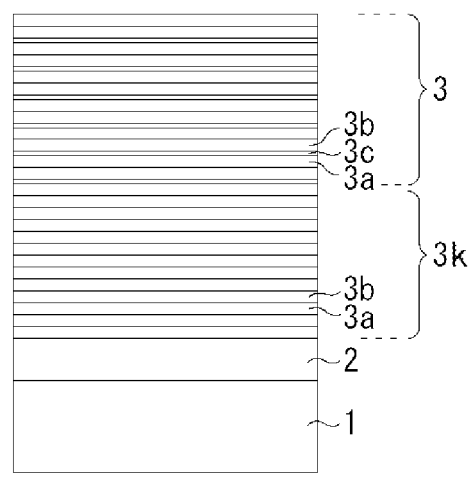
FIG. 16 illustrates a Sample including additional MQW layers for thickness check in Example 6: the Sample includes a GaSb substrate, a buffer layer, the additional MQW layers for thickness check, and an InAs/GaSb multiple quantum well including InSb strain-compensating layers.

FIG. 16 is an enlarged view of a portion of a semiconductor element of Example 6 according to an embodiment of the present invention. This portion includes additional MQW layers 3k for thickness check not including any InSb strain-compensating layer and a type-II InAs/GaSb multiple quantum well (main MQW layers) 3 including InSb strain-compensating layers 3c. The additional MQW layers 3k for thickness check do not include any InSb strain-compensating layer and hence the number of periods providing a thickness of more than the critical thickness causes relaxation of strain and collapse of the structure of the multiple quantum well. For this reason, the additional MQW layers 3k for thickness check were formed so as to have 6 periods of an InAs layer 3a and a GaSb layer 3b. Each InAs layer 3a had a thickness of 2 nm. Each GaSb layer 3b had a thickness of 4 nm. The type-II InAs/GaSb multiple quantum well (main MQW layers) 3 including InSb strain-compensating layers 3c was formed so as to have 100 periods of the InAs layer 3a (2 nm) and the GaSb layer 3b (4 nm) (the same film-thickness configuration as in the additional MQW layers 3k for thickness check).

Figure 17A:
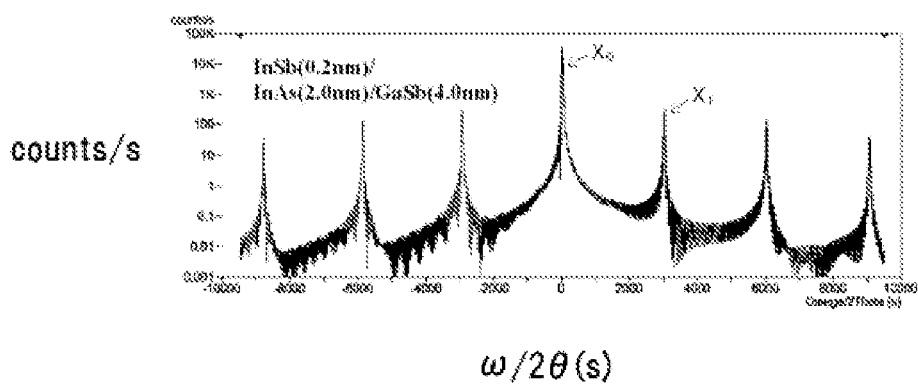
FIG. 17A illustrates a simulated XRD profile of a Sample having an InSb (0.2 nm)/InAs (2.0 nm)/GaSb (4.0 nm) multiple quantum well for the purpose of explaining the effect of additional MQW layers for thickness check.
Figure 17B:
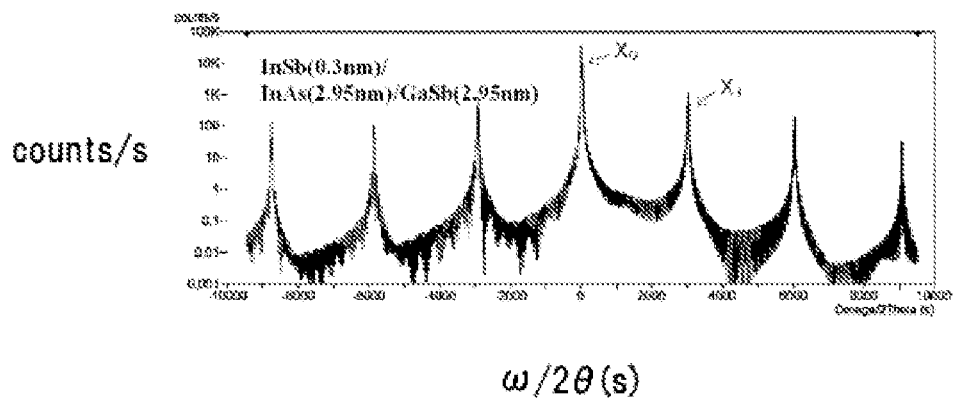
FIG. 17B illustrates a simulated XRD profile of a Sample having an InSb (0.3 nm)/InAs (2.95 nm)/GaSb (2.95 nm) multiple quantum well for the purpose of explaining the effect of additional MQW layers for thickness check.

FIGS. 17A and 17B are explanatory views indicating the importance of the presence of additional MQW layers 3k for thickness check not including any InSb film. FIGS. 17A and 17B illustrate simulated XRD profiles of the following Samples.

FIG. 17A: layered structure having 100 periods of InSb film (0.2 nm)/InAs layer (2.0 nm)/GaSb layer (4.0 nm)

FIG. 17B: layered structure having 100 periods of InSb film (0.3 nm)/InAs layer (2.95 nm)/GaSb layer (2.95 nm)

These two Samples have considerably different film-thickness configurations. However, as illustrated in FIGS. 17A and 17B, the two Samples provide almost the same XRD profiles. This means that use of an XRD profile alone is not sufficient for accurate determination or verification of film thicknesses of layers having a configuration of "InSb film having a thickness of about 1 ML/InAs layer/GaSb layer". For this reason, as illustrated in FIG. 16, it is important to use additional MQW layers 3k for thickness check including 10 or less periods of InAs layer/GaSb layer and not including any InSb layer.

In the growth of additional MQW layers 3k for thickness check including 10 or less periods of InAs layer/GaSb layer and not including any InSb film in FIG. 16, the InAs layers 3a and the GaSb layers 3b are desirably grown under the same growth conditions as in the growth of the InAs layers 3a and the GaSb layers 3b of the main MQW layers 3 including the InSb strain-compensating layers 3c. As a result, the InAs layers 3a and the GaSb layers 3b have the same film-thickness configuration both in the additional MQW layers 3k for thickness check and in the main MQW layers 3 including the InSb strain-compensating layers 3c. Even when the InAs layers 3a and the GaSb layers 3b are grown under different growth conditions between the additional MQW layers 3k for thickness check and the main MQW layers 3, as long as the relative relationship of growth rates between the additional MQW layers 3k and the main MQW layers 3 is known, the additional MQW layers 3k for thickness check are expected to provide the intended function.

Figure 18:
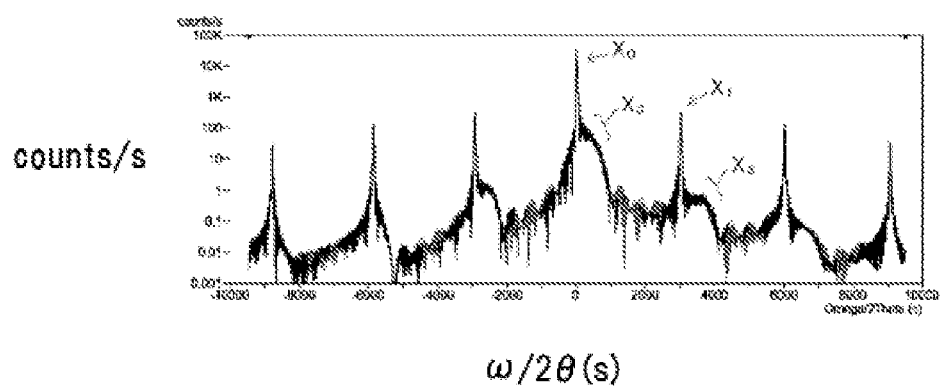
FIG. 18 illustrates a simulated XRD profile of a Sample having additional MQW layers for thickness check and an InAs/GaSb multiple quantum well including InSb strain-compensating layers.

FIG. 18 illustrates a simulated XRD profile of Sample (in FIG. 16) including the additional MQW layers 3k for thickness check and the main MQW layers 3. In this XRD profile, $X_o$ represents a peak derived from the GaSb substrate and $X_1$ represents a satellite peak derived from the main MQW layers 3 including the InSb strain-compensating layers 3c. XRD signals derived from the additional MQW layers 3k for thickness check appear in shoulder portions $X_3$ of the peaks $X_o$ and $X_1$. The film thicknesses of layers in the InAs layer 3a/GaSb layer 3b periodic structure including InSb layers 3c can be determined by the following procedures.

(1) From the XRD signals derived from the additional MQW layers 3k for thickness check, the film thicknesses of the InAs layer 3a and the GaSb layer 3b are determined.

(2) The film thicknesses of the InAs layer 3a and the GaSb layer 3b are thus fixed. The film thickness of the InSb strain-compensating layer 3c is then calculated by computer simulation so as to fit to the XRD profile in FIG. 18. Thus, the film thickness of the InSb strain-compensating layer 3c is determined.

The use of the above-described configuration of the semiconductor element and the procedures of X-ray diffractometry allows accurate determination of the film thicknesses of the InSb strain-compensating layer 3c, the GaSb layer 3b, and the InAs layer 3a in the main MQW layers 3.

INDUSTRIAL APPLICABILITY

The present invention can provide, for example, a semiconductor element including a type-II InAs/GaSb multiple quantum well that can be efficiently produced by metal-organic vapor phase epitaxy (MOVPE or MOCVD) and that has high crystallinity. In particular, an embodiment of the present invention is expected to contribute to the production of infrared photodiodes.

What is claimed is:

1. A semiconductor element including III-V compound semiconductors formed on a III-V compound semiconductor substrate, the semiconductor element comprising:
    a buffer layer disposed on the substrate;
    a first multiple quantum well disposed on the buffer layer, the first multiple quantum well including a GaSb layer and an InAs layer that are alternately stacked and a strain-compensating layer that is disposed on a lower-surface side or an upper-surface side of the InAs layer so as to be in contact with the InAs layer; and
    a second multiple quantum well including a GaSb layer and an InAs layer that are alternately stacked so as to be in contact with each other, the second multiple quantum well not including any strain-compensating layer on a lower-surface side or an upper-surface side of the InAs layer.

2. The semiconductor element according to claim 1, wherein the second multiple quantum well has a thickness equal to or less than a critical thickness.

3. The semiconductor element according to claim 1, wherein the second multiple quantum well includes 4 or more and 10 or less periods of the InAs layer and the GaSb layer.

4. The semiconductor element according to claim 1, wherein the substrate is a GaSb substrate.

5. The semiconductor element according to claim 1, wherein the buffer layer is a GaSb layer and the substrate is formed of GaSb or a III-V compound semiconductor that is not GaSb.

6. The semiconductor element according to claim 1, wherein the strain-compensating layer contains InSb, InAsSb, or InGaSb.

* * * * *